United States Patent [19]

Lunn

[11] 4,329,454
[45] May 11, 1982

[54] CEPHALOSPORIN COMPOUNDS

[75] Inventor: William H. W. Lunn, Indianapolis, Ind.

[73] Assignee: Eli Lilly and Company, Indianapolis, Ind.

[21] Appl. No.: 814,830

[22] Filed: Jul. 12, 1977

Related U.S. Application Data

[63] Continuation-in-part of Ser. No. 651,083, Jan. 21, 1976, abandoned, which is a continuation-in-part of Ser. No. 583,924, Jun. 10, 1975, abandoned, which is a continuation-in-part of Ser. No. 494,148, Aug. 2, 1974, abandoned.

[51] Int. Cl.³ ............................................. C07D 501/36
[52] U.S. Cl. ...................................... 544/026; 544/27; 424/246; 544/21
[58] Field of Search ...................... 544/30, 28, 26, 27; 424/246

[56] References Cited

U.S. PATENT DOCUMENTS 4,018,921  4/1977  Gleason ................................ 544/26
4,039,535  8/1977  Cooper ................................. 544/26
4,091,211  5/1978  Montavon et al. ................... 544/21

Primary Examiner—Nicholas S. Rizzo
Attorney, Agent, or Firm—William B. Scanlon; Arthur R. Whale

[57] ABSTRACT

Compounds of the formula

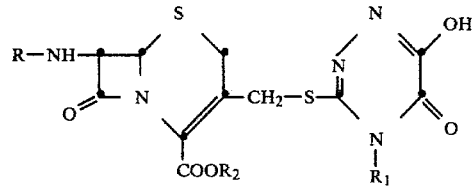

in which R is hydrogen or an acyl group, $R_1$ is hydrogen or lower alkyl, and $R_2$ is hydrogen, an alkali metal cation, or a readily removable ester forming group, are active antibiotics or intermediates thereto.

14 Claims, No Drawings

CEPHALOSPORIN COMPOUNDS

CROSS REFERENCE

This is a continuation-in-part of application Ser. No. 651,083 filed Jan. 21, 1976 now abandoned, which is a continuation-in-part of application Ser. No. 583,924 filed June 10, 1975, now abandoned, which is a continuation-in-part of application Ser. No. 494,148, filed Aug. 2, 1974, now abandoned.

BACKGROUND AND SUMMARY OF THE INVENTION

This invention relates to a new class of cephalosporin compounds. In particular, this invention relates to certain of such cephalosporins having in the 3-position a 5-oxo-6-hydroxy-4,5-dihydro-1,2,4-triazin-3-ylthiomethyl group. The compounds of this invention have excellent broad spectrum gram-positive and gram-negative antibiotic activity.

Broadly, the compounds of this invention have the formula

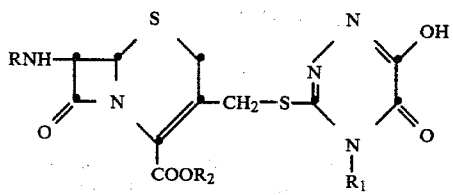

in which $R_1$ is hydrogen or lower alkyl; $R_2$ is hydrogen, an alkali metal cation, or a readily removable ester forming group; and R is hydrogen or the group $$R'-\overset{O}{\underset{\|}{C}}-$$

in which R' is hydrogen; $C_1$–$C_6$ alkyl; $C_1$–$C_3$ haloalkyl; $C_1$–$C_3$ cyanoalkyl; $C_1$–$C_3$ azidoalkyl; $C_1$–$C_3$ hydroxylkyl; p-nitrobenzyloxy; 4-amino-4-carboxybutyl; a 4-substituted-amino-4-carboxybutyl ester for the formula $$A-O-\overset{O}{\underset{\|}{C}}-\underset{\underset{A'}{\overset{|}{NH}}}{\overset{|}{CH}}-(CH_2)_2-CH_2-$$

in which A is diphenylmethyl, p-nitrobenzyl, benzyl, 2,2,2-trichloroethyl, t-butyl, or p-methoxybenzyl, and A' is $C_2$–$C_4$ alkanoyl, $C_2$–$C_4$ haloalkanoyl, benzoyl, halobenzoyl, 2,4-dinitrophenyl, or phthaloyl; or R' is a group of the formula $$\underset{a'}{\overset{a}{\bigcirc}}-(Z)_m-CH_2-$$

in which a and a' independently are hydrogen, $C_1$–$C_4$ lower alkyl, $C_1$–$C_4$ lower alkoxy, halogen, hydroxy, or aminomethyl;
Z is O or S; and
m is 0 or 1;
or R' is a group of the formula $$\underset{Q}{\overset{P-CH-}{|}}$$

in which P is 2-thienyl, 3-thienyl, 1-tetrazyl, or a phenyl group of the formula $$\underset{a'}{\overset{a}{\bigcirc}}$$

in which
a and a' are as defined above; and
Q is hydroxy, formyloxy, acetoxy, carboxy, sulfo, amino, or —NHY in which Y is benzyloxycarbonyl, t-butyloxycarbonyl, $$-\overset{O}{\underset{\|}{C}}-NH-\underset{\underset{NH}{\overset{\|}{}}}{C}-NH_2, \text{ or } -\overset{O}{\underset{\|}{C}}-\underset{\underset{}{\overset{R'''}{|}}}{N}-\overset{O}{\underset{\|}{C}}-V$$

in which R''' is hydrogen or $C_1$–$C_3$ alkyl, and V is phenyl, halophenyl, furyl, mono- or di-($C_1$–$C_3$ alkyl)amino, mono- or diphenylamino, or R''' and V taken together form a heterocycle, R''' being —$(CH_2)_n$— in which n is 2 or 3, and V being —NR''''—, in which R'''' is hydrogen, methanesulfonyl, or $C_1$–$C_3$ alkyl; or R' is a group of the formula R''—CH₂— in which R'' is 2-thienyl; 3-thienyl; 2-furyl; 2-oxazyl; 2-thiazyl; 1-tetrazyl; benzotriazolyl; 1,3,4-thiadiazolyl-2-thio; 1,2,5-thiadiazolyl-3-thio; 1,3,4-oxadiazolyl-2-thia; pyridylthia; 1-(4-cyano)-1,2,3-triazolyl; or 1-(3-cyano)-1,2,4-triazolyl.

DETAILED DESCRIPTION OF THE INVENTION

As hereinbefore indicated, the compounds of this invention have the formula

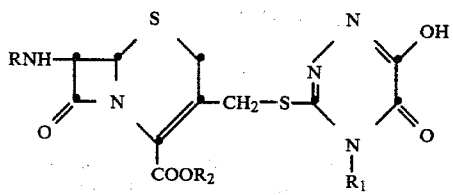

$R_1$ in formula I is hydrogen or lower alkyl. By "lower alkyl" is meant an alkyl group having from 1 to 4 carbon atoms, for example, methyl, ethyl, n-propyl, isopropyl, n-butyl, sec-butyl, isobutyl, and the like. Preferably, $R_1$ is methyl or ethyl, and, more preferably, $R_1$ is methyl.

Examples of the resulting 3-substituent of the cephalosporin in which $R_1$ is as defined above include 5-oxo-6-hydroxy-4,5-dihydro-1,2,4-triazin-3-ylthiomethyl; 4- methyl-5-oxo-6-hydroxy-4,5-dihydro-1,2,4-triazin-3-ylthiomethyl; 4-ethyl-5-oxo-6-hydroxy-4,5-dihydro-1,2,4-triazia-3-ylthiomethyl; 4-n-propyl-5-oxo-6-hydroxy-4,5-dihydro-1,2,4-triazin-3-ylthiomethyl; 4-isopropyl-5-oxo-6-hydroxy-4,5-dihydro-1,2,4-triazin-3-ylthiomethyl; 4-n-butyl-5-oxo-6-hydroxy-4,5-dihydro-1,2,4-triazin-3-ylthiomethyl; 4-sec-butyl-5-oxo-6-hydroxy-4,5-dihydro-1,2,4-triazin-3-ylthiomethyl; 4-isobutyl-5-oxo-6-hydroxy-4,5-dihydro-1,2,4-triazin-3-ylthiomethyl; and the like.

$R_2$ of formula I is hydrogen, an alkali metal cation, such as lithium, sodium, or potassium, or a readily removable ester forming group. The term "a readily removable ester forming group" refers to the commonly employed carboxylic acid protecting groups used to block the $C_4$ carboxylic acid group of the cephalosporin molecule. Such groups are readily removable by conventional techniques, and include, for example, $C_4$-$C_6$ tert-alkyl, $C_5$-$C_6$ tert-alkenyl, $C_5$-$C_6$ tert-alkynyl, benzyl, diphenylmethyl, p-nitrobenzyl, p-methoxybenzyl, 2,2,2-trichloroethyl, phenacyl, trimethylsilyl, $C_1$-$C_5$ alkanoyloxymethyl, phthalidyl, and other like cleavable moieties.

Examples of $C_4$-$C_6$ tert-alkyl groups include, for example, t-butyl, t-amyl, and t-hexyl. Examples of $C_5$-$C_6$ tert-alkenyl groups are t-pentenyl and t-hexenyl. Examples of $C_5$-$C_6$ tert-alkynyl groups are t-pentynyl and t-hexynyl.

When $R_2$ is a readily removable ester forming group, it is preferred that it be t-butyl, diphenylmethyl, benzyl, p-nitrobenzyl, p-methoxybenzyl, 2,2,2-trichloroethyl, trimethylsilyl, acetoxymethyl, pivaloyloxymethyl, or phthalidyl. Most preferably, when $R_2$ is a readily removable ester forming group, it is p-nitrobenzyl, acetoxymethyl, or pivaloyloxymethyl.

Most preferably, however, $R_2$ is hydrogen or an alkali metal cation. These $R_2$ substituents define those compounds of this invention which are most active antibiotically.

Cleavage of the ester moiety to the free 4-carboxyl function is desirable to produce a cephalosporin in which $R_2$ is hydrogen or an alkali metal cation. Cleavage is accomplished by conventional treatment. This includes, for example, treatment of the ester with an acid such as trifluoroacetic acid, hydrochloric acid, and the like, or with zinc and acid, such as formic acid, acetic acid, hydrochloric acid, and the like. Cleavage likewise can be accomplished by hydrogenating the ester in the presence of palladium, rhodium, or a compound thereof, in suspension or on a carrier such as barium sulfate, carbon, alumina, or the like.

As hereinbefore defined, this invention is directed to novel cephalosporin compounds represented by the general Formula I in which the substituent in the 7-position has the formula R—NH— in which R is hydrogen or the group

In the foregoing definition of the group R', the term "$C_1$-$C_6$ alkyl" refers to straight and branched chain alkyl hydrocarbon groups such as methyl, ethyl, n-propyl, isopropyl, n-butyl, sec-butyl, n-amyl, isoamyl, n-hexyl, 2,3-dimethylbutyl, and the like. The term "$C_1$-$C_3$ haloalkyl" refers to such groups as chloromethyl, bromomethyl, 2-iodoethyl, 2-chloropropyl, 3-bromopropyl, and the like. The term "$C_1$-$C_3$ cyanoalkyl" refers to such groups as cyanomethyl, 2-cyanoethyl, 3-cyanopropyl, 2-cyanopropyl, and the like. The term "$C_1$-$C_3$ azidoalkyl" refers to such groups as azidomethyl, 2-azidoethyl, 3-azidopropyl, 2-azidopropyl, and the like. The term "$C_1$-$C_3$ hydroxyalkyl" refers to such groups as hydroxymethyl, 2-hydroxyethyl, 3-hydroxypropyl, 2-hydroxypropyl, and the like.

In defining the 4-substituted-amino-4-carboxybutyl ester group, the term A' includes the groups "$C_2$-$C_4$ alkanoyl", "$C_2$-$C_4$ haloalkanoyl", and "halobenzoyl". The term "$C_2$-$C_4$ alkanoyl" refers to acetyl, propionyl, butyryl, and the like. The term "$C_2$-$C_4$ haloalkanoyl" refers to chloroacetyl, bromoacetyl, 2-chloropropionyl, 3-bromobutyryl, and the like. The term "halobenzoyl" refers to chloro and bromo substituted benzoyl groups such as 4-chlorobenzoyl, 4-bromobenzoyl, 2,4-dichlorobenzoyl, and the like.

As used herein, the term "halogen" and the term "halo" each refers to fluoro, chloro, bromo, or iodo. The term "$C_1$-$C_4$ lower alkyl" refers to the straight and branched chain lower aklkyl hydrocarbon groups such as methyl, ethyl, n-propyl, isopropyl, n-butyl, t-butyl, and the like. The term "$C_1$-$C_4$ lower alkoxy" refers to methoxy, ethoxy, isopropoxy, n-butoxy, and the like.

The following are illustrative of the group

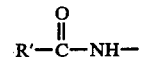

in Formula I above: formamido, acetamido, propionamido, butyramido, α-methylpropionamido, valeramido, α-methylbutyramido, trimethylacetamido, caproamido, heptylamido, chloroacetamido, bromoacetamido, fluoroacetamido, iodoacetamido, β-chloropropionamido, β-bromopropionamido, β-chlorobutyramido, γ-fluorobutyramido, cyanoacetamido, α-cyanopropionamido, β-cyanopropionamido, γ-cyanobutyramido, azidoacetamido, β-azidopropionamido, γ-azidobutyramido, β-azidobutyramido, hydroxyacetamido, α-hydroxypropionamido, β-hydroxybutyramido, p-nitrobenzyloxycarbamido, 5-amino-5-carboxyvaleramido, 5-(diphenylmethoxycarbonyl)-5-(acetamido)-valeramido, 5-(p-nitrobenzyloxycarbonyl)-5-(2,4-dichlorobenzamido)valeramido, and the like.

The following are illustrative of the groups

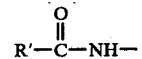

in the above definition in which R' is

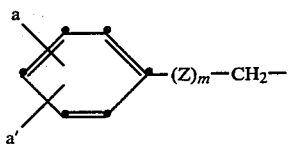

and in which m is 0: phenylacetamido, 4-methylphenylacetamido, 3-ethylphenylacetamido, 4-isopropylphenylacetamido, 2-methylphenylacetamido, 4-chlorophenylacetamido, 4-nitrophenylacetamido, 4-bromophenylacetamido, 2,4-dichlorophenylacetamido, 3-bromophenylacetamido, 4-fluorophenylacetamido, 2-fluorophenylacetamido, 3,4-dihydroxyphenylacetamido, 4-hydroxyphenylacetamido, 3-hydroxyphenylacetamido, 2,6-dimethoxyphenylacetamido, 3-methoxyphenylacetamido, 4-isopropoxyphenylacetamido, 3-ethoxyphenylacetamido, 4-methoxyphenylacetamido, 3,4-dimethoxyphenylacetamido, 4-t-butoxyphenylacetamido, 2-aminomethylphenylacetamido, 4-aminomethylphenylacetamido, 3-n-butoxyphenylacetamido, 3-chloro-4-methylphenylacetamido, 3-nitrophenylacetamido, and the like. When, in the above formula, m=1 and Z represents —O—, illustrative groups include the following: phenoxyacetamido, 4-methylphenoxyacetamido, 3-ethylphenoxyacetamido, 4-isopropylphenoxyacetamido, 2-methylphenoxyacetamido, 4-chlorophenoxyacetamido, 4-nitrophenoxyacetamido, 4-bromophenoxyacetamido, 2,4-dichlorophenoxyacetamido, 3-bromophenoxyacetamido, 4-fluorophenoxyacetamido, 2-fluorophenoxyacetamido, 3,4-dihydroxyphenoxyacetamido, 4-hydroxyphenoxyacetamido, 3-hydroxyphenoxyacetamido, 2,6-dimethoxyphenoxyacetamido, 3-ethoxyphenoxyacetamido, 4-methoxyphenoxyacetamido, 3,4-dimethoxyphenoxyacetamido, 4-t-butoxyphenoxyacetamido, 2-n-butoxyphenoxyacetamido, 3-chloro-4-methylphenoxyacetamido, 3-nitrophenoxyacetamido, 3-hydroxy-4-methylphenoxyacetamido, 2-chlorophenoxyacetamido, 3-hydroxy-4-methylphenoxyacetamido, 2-chlorophenoxyacetamido, 4-isopropoxyphenoxyacetamido, 2-aminomethylphenoxyacetamido, 4-aminomethylphenoxyacetamido, and the like. When, in the foregoing formula, m=1 and Z represents —S—, illustrative groups include the following: phenylmercaptoacetamido, 4-methylphenylmercaptoacetamido, 3-ethylphenylmercaptoacetamido, 4-isopropylphenylmercaptoacetamido, 2-methylphenylmercaptoacetamido, 4-chlorophenylmercaptoacetamido, 4-nitrophenylmercaptoacetamido, 4-bromophenylmercaptoacetamido, 2,4-dichlorophenylmercaptoacetamido, 3-bromophenylmercaptoacetamido, 4-fluorophenylmercaptoacetamido, 2-fluorophenylmercaptoacetamido, 3,4-dihydroxyphenylmercaptoacetamido, 4-hydroxyphenylmercaptoacetamido, 3-hydroxyphenylmercaptoacetamido, 2,6-dimethoxyphenylmercaptoacetamido, 3-ethoxyphenylmercaptoacetamido, 4-methoxyphenylmercaptoacetamido, 3,4-dimethylphenylmercaptoamido, 4-t-butoxyphenylmercaptoacetamido, 3-n-butoxyphenylmercaptoacetamido, 3-chloro-4-methylphenylmercaptoacetamido, 3-nitrophenylmercaptoacetamido, 3,4-dimethylphenylmercaptoacetamido, 3,4-dichlorophenylmercaptoacetamido, 2,5-dichlorophenylmercaptoacetamido, 3-fluoro-4-chlorophenylmercaptoacetamido, 3-chloro-4-fluorophenylmercaptoacetamido, 2,6-difluorophenylmercaptoacetamido, 3-fluorophenylmercaptoacetamido, 2-aminomethylphenylmercaptoacetamido, 4-aminomethylphenylmercaptoacetamido, and such like groups.

When R' represents a group of the formula

illustrative groups having the overall formula

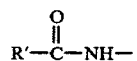

include the mandelamido group of the formula

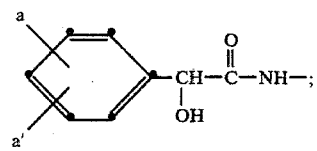

the O-formyl and O-acetyl derivatives thereof represented by the general formula

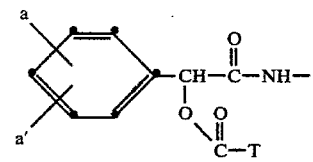

in which T is hydrogen or methyl; the α-carboxyphenylacetamido group represented by the formula

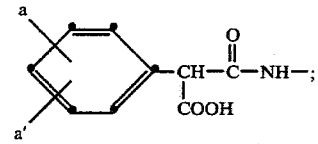

the α-sulfophenylacetamido group represented by the formula

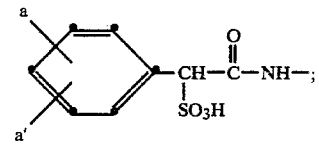

the α-aminophenylacetamido group represented by the formula

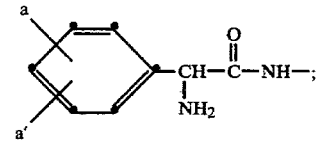

or the α-(substituted-amino)phenylacetamido group represented by the formula

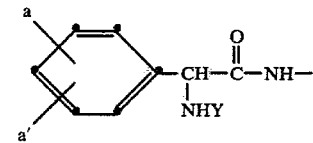

in which Y is benzyloxycarbonyl, t-butyloxycarbonyl,

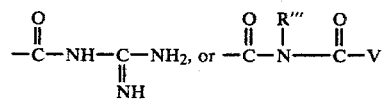

in which V is, for example, phenyl, halophenyl, furyl, monomethylamino, dimethylamino, monoethylamino, diethylamino, methylethylamino, n-propylamino, di-n-propylamino, di-isopropylamino, phenylamino, diphenylamino, and the like. Moreover, in any of the above, R''' can be hydrogen or $C_1$–$C_3$ alkyl, specifically methyl, ethyl, n-propyl or isopropyl. R''' and V can, together with the group to which they are attached, form a heterocycle such that Y has the structure

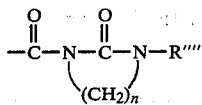

in which n is 2 or 3 and R'''' is hydrogen, methanesulfonyl, or $C_1$–$C_3$ alkyl. Also included are those α-substituted 2-thienylacetamido, 3-thienylacetamido, and 1-tetrazylacetamido groups in which, in the above formulae, the phenyl group is replaced by a 2-thienyl, a 3-thienyl, or a 1-tetrazyl ring.

Illustrative of the foregoing acetamido groups are 4-methylmandelamido, 4-hydroxymandelamido, 3-hydroxymandelamido, 4-methoxymandelamido, 3-bromomandelamido, mandelamido, 4-chloromandelamido, 3-methyl-4-fluoromandelamido, 2-fluoromandelamido, 4-fluoromandelamido, 4-isopropylmandelamido, 3,4-dimethyl-O-formylmandelamido, 4-chloro-O-formylmandelamido, 3-isopropoxy-O-formylmandelamido, 3-bromo-O-formylmandelamido, O-formylmandelamido, 3,4-dimethoxy-O-formylmandelamido, O-acetylmandelamido, 4-hydroxy-O-acetylmandelamido, α-hydroxy-2-thienylacetamido, α-hydroxy-3-thienylacetamido, α-formyloxy-2-thienylacetamido, α-acetoxy-2-thienylacetamido, α-formyloxy-3-thienylacetamido, α-acetoxy-3-thienylacetamido, α-hydroxy-1-tetrazylacetamido, α-formyloxy-1-tetrazylacetamido, α-acetoxy-1-tetrazylacetamido, α-carboxyphenylacetamido, α-carboxy-4-methylphenylacetamido, α-carboxy-4-hydroxyphenylacetamido, α-carboxy-3-hydroxyphenylacetamido, α-carboxy-4-methoxyphenylacetamido, α-carboxy-3-bromophenylacetamido, α-carboxy-4-chlorophenylacetamido, α-carboxy-3-methyl-4-fluorophenylacetamido, α-carboxy-2-fluorophenylacetamido, α-carboxy-4-fluorophenylacetamido, α-carboxy-4-isopropylphenylacetamido, α-carboxy-3,4-dimethylphenylacetamido, α-carboxy-3-isopropoxyphenylacetamido, α-carboxy-3,4-dimethoxyphenylacetamido, α-carboxy-2-thienylacetamido, α-carboxy-3-thienylacetamido, α-carboxy-1-tetrazylacetamido, α-sulfophenylacetamido, α-sulfo-4-methylphenylacetamido, α-sulfo-4-hydroxyphenylacetamido, α-sulfo-3-hydroxyphenylacetamido, α-sulfo-4-methoxyphenylacetamido, α-sulfo-3-bromophenylacetamido, α-sulfo-4-chlorophenylacetamido, α-sulfo-3-methyl-4-fluorophenylacetamido, α-sulfo-2-fluorophenylacetamido, α-sulfo-4-fluorophenylacetamido, α-sulfo-4-isopropylphenylacetamido, α-sulfo-3,4-dimethylphenylacetamido, α-sulfo-3-isopropoxyphenylacetamido, α-sulfo-3,4-dimethoxyphenylacetamido, α-sulfo-2-thienylacetamido, α-sulfo-3-thienylacetamido, α-sulfo-1-tetrazylacetamido, α-aminophenylacetamido, α-amino-4-methylphenylacetamido, α-amino-4-hydroxyphenylacetamido, α-amino-3-hydroxyphenylacetamido, α-amino-4-methoxyphenylacetamido, α-amino-3-bromophenylacetamido, α-amino-4-chlorophenylacetamido, α-amino-3-chloro-4-hydroxyphenylacetamido, α-amino-2-fluorophenylacetamido, α-amino-4-fluorophenylacetamido, α-amino-4-isopropylphenylacetamido, α-amino-3,4-dimethylphenylacetamido, α-amino-3-isopropoxyphenylacetamido, α-amino-3,4-dimethoxyphenylacetamido, α-amino-2-thienylacetamido, α-amino-3-thienylacetamido, α-amino-1-tetrazylacetamido, α-(3-guanyl-1-ureido)-phenylacetamido, α-(3-methylaminocarbonyl-1-ureido)phenylacetamido, α-(3-dimethylaminocarbonyl-3-methyl-1-ureido)phenylacetamido, α-[N-(imidazolidine-2-one-1-ylcarbonyl)amino]phenylacetamido, α-[N-(3-methylimidazolidine-2-one-1-ylcarbonyl)amino]phenylacetamido; α-[N-(3-methanesulfonylimidazolidine-2-one-1-ylcarbonyl)amino]phenylacetamido; α-[N-(hexahydropyrimidine-2-one-1-ylcarbonyl)amino]phenylacetamido; α-[N-(3-methylhexahydropyrimidine-2-one-1-ylcarbonyl)amino]phenylacetamido; α-[N-(3-methanesulfonylhexahydropyrimidine-2-one-1-ylcarbonyl)amino]phenylacetamido; α-(3-phenylacetaminocarbonyl-3-propyl-1-ureido)-phenylacetamido, α-(3-di-n-propylaminocarbonyl-1-ureido)phenylacetamido, and the like.

Illustrative of the group

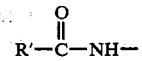

in the above definition in which R' is R''—CH$_2$— are the following: 2-thienylacetamido, 3-thienylacetamido, 2-furylacetamido, oxazyl-2-acetamido, thiazyl-2-acetamido, tetrazyl-1-acetamido, benzotriazolylacetamido, 1,3,4-thiadiazolyl-2-thioacetamido, 1,2,5-thiadiazolyl-3-thioacetamido, 1,3,4-oxadiazolyl-2-thioacetamido, pyridylthioacetamido, 4-(cyano)-1,2,3-triazolyl-1-acetamido, and 3-(cyano)-1,2,4-triazolyl-1-acetamido.

A preferred group of cephalosporins of this invention are represented by the following formula II

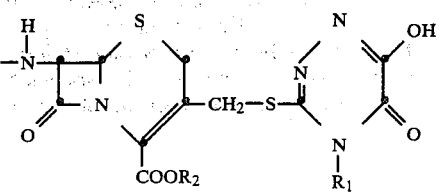

in which $R_1$, $R_2$, a, a', Z and m have the same meanings as defined above. Illustrative of these preferred compounds presented in the form of their free acid are the following: 7-phenylacetamido-3-(4-methyl-5-oxo-6-hydroxy-4,5-dihydro-1,2,4-triazin-3-ylthio)methyl-3- cephem-4-carboxylic acid, 7-phenoxyacetamido-3-(4-ethyl-5-oxo-6-hydroxy-4,5-dihydro-1,2,4-triazin-3-ylthio)methyl-3-cephem-4-carboxylic acid, 7-(4-hydroxyphenylacetamido)-3-(5-oxo-6-hydroxy-4,5-dihydro-1,2,4-triazin-3-ylthio)methyl-3-cephem-4-carboxylic acid, 7-(4-chlorophenoxyacetamido)-3-(4-n-propyl-5-oxo-6-hydroxy-4,5-dihydro-1,2,4-triazin-3-ylthio)methyl-3-cephem-4-carboxylic acid, 7-(4-methoxyphenoxyacetamido)-3-(4-methyl-5-oxo-6-hydroxy-4,5-dihydro-1,2,4-triazin-3-ylthio)methyl-3-cephem-4-carboxylic acid, 7-(2,5-dichlorophenylthioacetamido)-3-(4-isopropyl-5-oxo-6-hydroxy-4,5-dihydro-1,2,4-triazin-3-ylthio)methyl-3-cephem-4-carboxylic acid, 7-phenylthioacetamido-3-(4-n-butyl-5-oxo-6-hydroxy-4,5-dihydro-1,2,4-triazin-3-ylthio)methyl-3-cephem-4-carboxylic acid, and the like.

Another preferred group of cephalosporins of this invention are those represented by the following formula III:

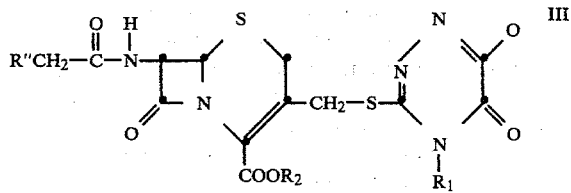

in which R" represents 2-thienyl, 3-thienyl, 2-furyl, or 1-tetrazyl, and $R_1$ and $R_2$ have the same meaning as defined above. Illustrative of the foregoing compounds represented by the formula III and presented as their free acid are the following:

7-(2-thienylacetamido)-3-(4-methyl-5-oxo-6-hydroxy-4,5-dihydro-1,2,4-triazin-3-ylthio)methyl-3-cephem-4-carboxylic acid, 7-(2-furylacetamido)-3-(4-ethyl-5-oxo-6-hydroxy-4,5-dihydro-1,2,4-triazin-3-ylthiomethyl)-3-cephem-4-carboxylic acid, 7-(3-thienylacetamido)-3-(4-sec-butyl-5-oxo-6-hydroxy-4,5-dihydro-1,2,4-triazin-3-ylthio)methyl-3-cephem-4-carboxylic acid, 7-(1-tetrazylacetamido)-3-(4-methyl-5-oxo-6-hydroxy-4,5-dihydro-1,2,4-triazin-3-ylthio)methyl-3-cephem-4-carboxylic acid, 7-(1-tetrazylacetamido)-3-(4-ethyl-5-oxo-6-hydroxy-4,5-dihydro-1,2,4-triazin-3-ylthio)methyl-3-cephem-4-carboxylic acid, 7-(2-thienylacetamido)-3-(4-ethyl-5-oxo-6-hydroxy-4,5-dihydro-1,2,4-triazin-3-ylthio)methyl-3-cephem-4-carboxylic acid, and the like.

A further preferred group of cephalosporins of this invention are those represented by the following formula IV

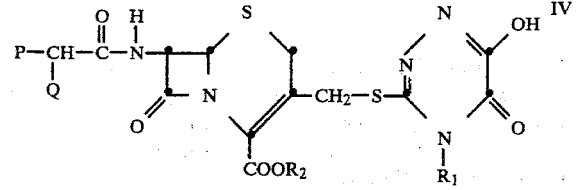

wherein P represents 1-tetrazyl, phenyl, or a substituted phenyl group as defined herein and Q is hydroxy, formyloxy, acetoxy, carboxy, or amino. Illustrative of the foregoing compounds represented by formula IV and presented as their free acid are the following:

7-mandelamido-3-(4-methyl-5-oxo-6-hydroxy-4,5-dihydro-1,2,4-triazin-3-ylthio)methyl-3-cephem-4-carboxylic acid, 7-(4-chloromandelamido)-3-(5-oxo-6-hydroxy-4,5-dihydro-1,2,4-triazin-3-ylthio)methyl-3-cephem-4-carboxylic acid, 7-(4-hydroxymandelamido)-3-(4-ethyl-5-oxo-6-hydroxy-4,5-dihydro-1,2,4-triazin-3-ylthio)methyl-3-cephem-4-carboxylic acid, 7-(4-methoxymandelamido)-3-(4-n-propyl-5-oxo-6-hydroxy-4,5-dihydro-1,2,4-triazin-3-ylthio)methyl-3-cephem-4-carboxylic acid, 7-[α-(hydroxy)-1-tetrazylacetamido]-3-(4-methyl-5-oxo-6-hydroxy-4,5-dihydro-1,2,4-triazin-3-ylthio)methyl-3-cephem-4-carboxylic acid, 7-(α-formyloxyphenylacetamido)-3-(4-ethyl-5-oxo-6-hydroxy-4,5-dihydro-1,2,4-triazin-3-ylthio)methyl-3-cephem-4-carboxylic acid, 7-(α-acetoxyphenylacetamido)-3-(4-isobutyl-5-oxo-6-hydroxy-4,5-dihydro-1,2,4-triazin-3-ylthio)methyl-3-cephem-4-carboxylic acid, 7-(α-carboxyphenylacetamido)-3-(4-methyl-5-oxo-6-hydroxy-4,5-dihydro-1,2,4-triazin-3-ylthio)methyl-3-cephem-4-carboxylic acid, 7-[α-(carboxy)-4-hydroxyphenylacetamido]-3-(4-ethyl-5-oxo-6-hydroxy-4,5-dihydro-1,2,4-triazin-3-ylthio)methyl-3-cephem-4-carboxylic acid, 7-[α-(carboxy)-4-chlorophenylacetamido]-3-(4-n-propyl-5-oxo-6-hydroxy-4,5-dihydro-1,2,4-triazin-3-ylthio)methyl-3-cephem-4-carboxylic acid, 7-[α-(carboxy)-1-tetrazylacetamido]-3-(4-methyl-5-oxo-6-hydroxy-4,5-dihydro-1,2,4-triazin-3-ylthio)methyl-3-cephem-4-carboxylic acid, 7-(α-aminophenylacetamido)-3-(4-methyl-5-oxo-6-hydroxy-4,5-dihydro-1,2,4-triazin-3-ylthio)methyl-3-cephem-4-carboxylic acid, 7-(α-aminophenylacetamido)-3-(4-ethyl-5-oxo-6-hydroxy-4,5-dihydro-1,2,4-triazin-3-ylthio)methyl-3-cephem-4-carboxylic acid, 7-[α-(amino)-1-tetrazylacetamido]-3-(4-methyl-5-oxo-6-hydroxy-4,5-dihydro-1,2,4-triazin-3-ylthio)methyl-3-cephem-4-carboxylic acid, 7-[α-(amino)-4-hydroxyphenylacetamido]-3-(4-ethyl-5-oxo-6-hydroxy-4,5-dihydro-1,2,4-triazin-3-ylthio)methyl-3-cephem-4-carboxylic acid, 7-[α-(amino)-4-chlorophenylacetamido]-3-(4-ethyl-5-oxo-6-hydroxy-4,5-dihydro-1,2,4-triazin-3-ylthio)methyl-3-cephem-4-carboxylic acid, and the like.

Another preferred group of cephalosporins of this invention are those represented by the following formula V

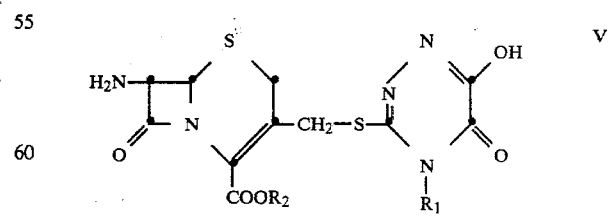

These structures are highly useful as intermediates in preparing other compounds of this invention. They are readily convertible to other compounds by routine acylation procedures by which the free amino substituent in the 7-position is acylated with any of the other herein defined acyl substituents. Illustrative of these compounds represented by formula V and presented as their free acid are the following:

7-amino-3-(5-oxo-6-hydroxy-4,5-dihydro-1,2,4-triazin-3-ylthio)methyl-3-cephem-4-carboxylic acid, 7-amino-3-(4-methyl-5-oxo-6-hydroxy-4,5-dihydro-1,2,4-triazin-3-ylthio)methyl-3-cephem-4-carboxylic acid, 7-amino-3-(4-ethyl-5-oxo-6-hydroxy-4,5-dihydro-1,2,4-triazin-3-ylthio)methyl-3-cephem-4-carboxylic acid, 7-amino-3-(4-n-propyl-5-oxo-6-hydroxy-4,5-dihydro-1,2,4-triazin-3-ylthio)methyl-3-cephem-4-carboxylic acid, 7-amino-3-(4-isopropyl-5-oxo-6-hydroxy-4,5-dihydro-1,2,4-triazin-3-ylthio)methyl-3-cephem-4-carboxylic acid, 7-amino-3-(4-n-butyl-5-oxo-6-hydroxy-4,5-dihydro-1,2,4-triazin-3-ylthio)methyl-3-cephem-4-carboxylic acid, 7-amino-3-(4-sec-butyl-5-oxo-6-hydroxy-4,5-dihydro-1,2,4-triazin-3-ylthio)methyl-3-cephem-4-carboxylic acid, 7-amino-3-(4-isobutyl-5-oxo-6-hydroxy-4,5-dihydro-1,2,4-triazin-3-ylthio)methyl-3-cephem-4-carboxylic acid, and the like.

The compounds of this invention can be prepared by well recognized cephalosporin preparative techniques. They are readily available by displacement of an acetoxy function present in the 3-position of a 3-acetoxymethyl cephalosporin compound. Thus, any of the cephalosporins of this invention can be prepared from the corresponding 3-acetoxymethyl cephalosporins by the well recognized displacement reaction. Thus, a typical sequence for preparing any of the compounds of this invention from readily available 7-aminocephalosporanic acid (7-ACA) can be as follows:

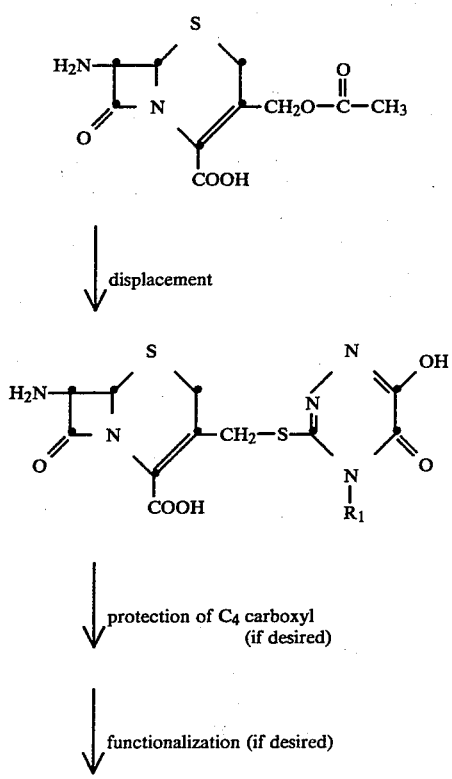

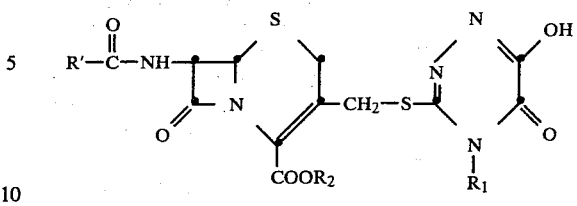

In accordance with the above scheme, the acetoxy function of 7-ACA is displaced with the defined triazinylthio derivative. The resulting product is the corresponding 7-amino cephalosporin, a compound of this invention. This compound can be converted by means of well recognized acylation techniques to any of the defined 7-acylamido cephalosporins of this invention.

The above sequence can be altered such that the 7-ACA is first acylated in the 7-position to produce the corresponding 7-acylamidocephalosporanic acid or ester thereof. The resulting product, if an ester, is then cleaved to remove the $C_4$ ester protecting group, and the resulting acid is then subjected to the displacement reaction to produce the compound of this invention. Any of these procedures used to accomplish these conversions are well recognized in the art.

The particular compound which is employed to displace the acetoxy function in the 3-position is a 3-mercapto-5-oxo-6-hydroxy-4,5-dihydro-1,2,4-triazine unsubstituted in the 4-position or suitably substituted in the 4-position with a lower alkyl group as herein defined. These 3-mercapto-1,2,4-triazines are prepared by a method described in Pesson et al., *Bulletin de la Societe Chemique de France*, (1970), pages 1590–1599. In accordance with the method described in this publication, the 1,2,4-triazine is obtained by reaction of a thiosemicarbazide with diethyl oxalate in the presence of sodium ethoxide. The sequence is as follows:

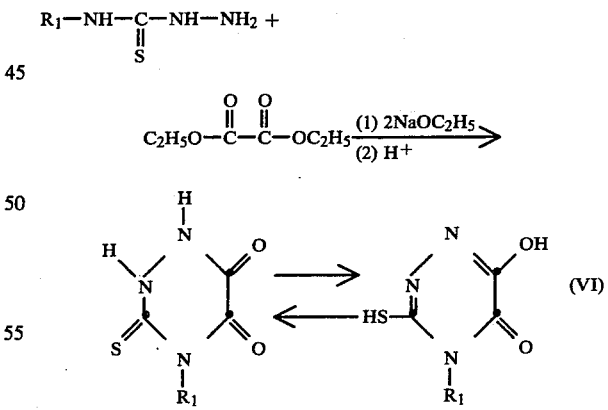

In the foregoing sequence, $R_1$ is hydrogen or lower alkyl as herein defined. As noted, the product exists in tautomeric forms. The tautomer aspect is detailed in Pesson et al., *Bulletin de la Societe Chimique de France*. (1970), pages 1599–1606.

Another method for obtaining the 3-mercapto-5-oxo-6-hydroxy-4,5-dihydro-1,2,4-triazine used to prepare the compounds of this invention involves treatment of an oxamic hydrazide with thiophosgene as follows:

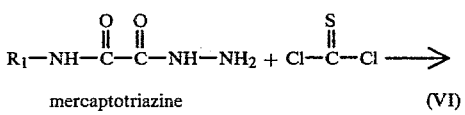

mercaptotriazine (VI)

$R_1$ in the foregoing reaction is hydrogen or lower alkyl. The reaction is carried out in an aqueous medium and in the presence of dilute acid to solubilize the oxamic hydrazide. This reaction was reported in Beckett, T. and Dyson, G. M., *J. Chem. Soc.* (1937), 1358. However, the correct structure of the product was not established until later, being reported in Anthoni et al., *Acta. Chem. Scand.* B30, No. 1, 71–82 (1976).

The aforementioned displacement reaction employed in preparing compounds of this invention comprises reacting the corresponding 3-acetoxymethyl compound preferably in a polar medium with the appropriate 3-mercapto-1,2,4-triazine derivative so as to displace the acetoxy group. The desired 3-substituted cephalosporin derivative is then recovered.

This reaction may conveniently be effected by maintaining the reactants in solution at a temperature such as, for example, from about 15° C. to about 100° C. and until the desired derivative is obtained in optimum yield. The reactants are advantageously employed in a ratio of about 1 molar equivalent of the 3-acetoxymethyl cephalosporin to form about one to about ten molar equivalents of the 3-mercapto-1,2,4-triazine. Preferably, the reaction is carried out using the molar equivalent amounts of these reactants or a moderate excess of the triazine compound. The pH of the reaction solution is advantageously maintained at from about 5.0 to about 8.0.

The reaction appears to proceed by a polar or ionic mechanism. It is preferred therefore to employ a polar medium for the reaction. This facilitates the ready on-going of the desired reaction. Water may be employed as the polar medium and, indeed, is preferred. Any other typical and well recognized polar solvents can be employed as well. It is also possible to employ as supporting medium for the reaction an excess of the displacing 3-mercapto-1,2,4-triazine derivative.

The resulting reaction product can be separated from the reaction mixture by a variety of methods including crystallization, ionophoresis, paper chromatography, chromatography on ion-exchange resins, and the like.

The displacement reaction can be applied either to 7-amino- or to a 7-acylamido cephalosporanic acid. When 7-ACA is employed, the resulting product can then be acylated. The acylation of the 7-amino group of cephalosporins is a well-known reaction and can be accomplished by reacting the cephalosporin with an acid halide or mixed anhydride representative of the desired acyl function. The particular method of acylation is not important to this invention.

The compounds of this invention are themselves antibiotically active and/or are intermediates to antibiotically active compounds. Those compounds which particularly exhibit antibiotic activity are those in which $R_2$ is hydrogen or an alkali metal cation. Compounds in which $R_2$ is other than hydrogen or an alkali metal cation are readily converted thereto by cleavage techniques hereinbefore described.

In the Table following, the minimum inhibitory concentrations (MIC) in micrograms per milliliter (mcg/ml) of compounds of this invention against a gram-negative organism, *Escherichia coli*, and against a gram-positive organism, penicillin-resistant *Staphylococcus aureus*, are provided. The MIC values were determined by the Gradient Plate technique described in Bryson and Szybalski, *Science*, 116, 45 (1952).

TABLE

Antibiotic Activity

R—NH—[β-lactam-S]—CH₂S—[triazine with $R_1$]—COOH / OH

| R | $R_1$ | E. Coli | S. aureus |
|---|---|---|---|
| | | \multicolumn{2}{c}{Minimum Inhibitory Conc. (mcg/ml)} |
| ClH . H— | $CH_3$ | 50 | 15 |
| H—CO— | $CH_3$ | 12.2 | 0.2 |
| 2,5-dichlorophenylthioacetyl | $CH_3$ | 20.5 | 0.6 |
| 2,5-dichlorophenylthioacetyl | $C_2H_5$ | 22.5 | 0.7 |
| α-hydroxyphenylacetyl | $CH_3$ | 4.0 | 0.7 |
| α-hydroxyphenylacetyl (Na salt) | $CH_3$ | 4.5 | 0.9 |
| α-formyloxyphenylacetyl | $CH_3$ | 3.5 | 4.0 |
| α-(t-butyloxycarbonylamino)phenylacetyl | $CH_3$ | 130 | 0.5 |
| α-aminophenylacetyl | $CH_3$ | 5.3 | 2.0 |
| 2-thienylacetyl | $CH_3$ | 1.5 | 0.3 |
| 2-thienylacetyl | $C_2H_5$ | 3.0 | 0.5 |
| 4-aminomethylphenylacetyl | $CH_3$ | 3.0 | 0.5 |
| α-[3-(4-chlorobenzoyl)-3-methyl-1-ureido]-phenylacetyl | $CH_3$ | 4.5 | 4.0 |
| α-(3-furoyl-1-ureido)-phenylacetyl | $CH_3$ | 8.3 | 7.0 |
| α-[3-(2-chlorobenzoyl)-3-methyl-1-ureido]phenylacetyl | $CH_3$ | 5.7 | 5.5 |
| 1H-tetrazole-acetyl | $CH_3$ | 0.8 | 0.5 |
| α-amino-4-hydroxyphenylacetyl | $CH_3$ | 3.0 | 4.0 |
| α-(3-methylaminocarbonyl-3-methyl-1-ureido)-phenylacetyl | $CH_3$ | 15.5 | 3.0 |
| α-(imidazolidine-2-one-1-yl-carbonylamino)-phenylacetyl | $CH_3$ | 19.0 | 2.0 |
| α-(3-methanesulfonylimidazolidine-2-one-1-ylcarbonylamino)phenylacetyl | $CH_3$ | 9.5 | 5.0 |
| α-(amino)thien-2-ylacetyl | $CH_3$ | 6.5 | 6.0 |
| α-(3-methyl-3-methylaminocarbonyl-1-ureido)thien-2-ylacetyl | $CH_3$ | 14.2 | 1.0 |
| α-(3-methanesulfonylimidazolidine-2-one-1-ylcarbonylamino)- | | | |

TABLE-continued
Antibiotic Activity $$\text{R—NH} \begin{array}{c} \text{S} \\ \text{N} \\ \text{O} \end{array} \text{CH}_2\text{S}-\begin{array}{c} \text{N} \\ \text{N} \\ \text{COOH} \end{array} \begin{array}{c} \text{OH} \\ \text{N} \\ \text{N} \\ \text{R}_1 \end{array} \text{O}$$

| R | $R_1$ | Minimum Inhibitory Conc. (mcg/ml) E. Coli | S. aureus |
|---|---|---|---|
| thien-2-yl-acetyl | $CH_3$ | 4.7 | 1.0 |
| α-[3-(2-chlorobenzoyl)-3-methyl-1-ureido]-4-hydroxyphenyl-acetyl | $CH_3$ | 11.1 | 0.7 |
| α-(3-methanesulfonylimidazolidine-2-one-1-yl-carbonylamino)-4-hydroxyphenyl-acetyl | $CH_3$ | 0.6 | 2.5 |
| α-(3-methylaminocarbonyl-3-methyl-1-ureido)-4-hydroxyphenyl-acetyl | $CH_3$ | 4.4 | 2.2 |
| α-(imidazolidine-2-one-1-ylcarbonylamino)-4-hydroxyphenyl-acetyl | $CH_3$ | 5.6 | 2.1 |
| 2-aminomethyl-phenylacetyl | $CH_3$ | 0.5 | 0.4 |
| α-(3-furoyl-1-ureido)-4-hydroxy-phenylacetyl | $CH_3$ | 5.0 | 0.8 |

The preparation of the compounds of this invention is illustrated by the following examples.

PREPARATION OF 3-MERCAPTO-4-METHYL-5-OXO-6-HYDROXY-4,5-DIHYDRO-1,2,4-TRIAZINE

To a 22 liter (l.) flask containing 12.5 l. of anhydrous ethanol maintained in a nitrogen atmosphere were slowly added 230 g. of sodium. The mixture was maintained at room temperature overnight, a slow, but constant, stream of nitrogen being admitted to the flask. The mixture then was heated to 50° C., and 1050 g. (10 mole) of 4-methylthiosemicarbazide were added. The temperature of the mixture fell to 40° C. To the mixture were then added 1530 g. of diethyl oxalate through a funnel. Addition was at a rate sufficient for the reaction mixture to attain a temperature of from about 60° C. to about 65° C. The temperature of the resulting mixture rose to 65° C. The mixture was refluxed with stirring for four hours during which time a precipitate formed. The precipitate changed in appearance during the period of reflux. Upon discontinuing heating and stirring, the white solid grandually settled to the bottom of the flask leaving a clear light yellow supernatant liquid. The mixture was allowed to stand overnight. The bulk of the clear supernatant was removed by suction, and the white crystalline product in the form of its sodium salt was removed from the residual mixture by filtration and washed with dry ethanol.

The product was dissolved in water, and the pH of the solution was adjusted to pH 5.5. A small amount of material was filtered off and discarded. The pH of the filtrate then was adjusted to 1.5, cooled, and filtered to obtain 211.5 g. of product, m.p. 212°–216° C.

EXAMPLE 1

To 36 ml. of water were added with stirring 1.44 g. of 3-mercapto-4-methyl-5-oxo-6-hydroxy-4,5-dihydro-1,2,4-triazine and 8.5 ml. of 1 N sodium hydroxide. The pH of the resulting mixture was 8.3, and the pH was lowered to 7.6 by addition of dilute acid. 7-α-(t-Butoxycarbonylamino)phenylacetamido-3-acetoxymethyl-3-cephem-4-carboxylic acid (4.5 g., 9 mmole.) was added to the mixture with stirring, and the pH of the resulting mixture adjusted to 6.9 as the cephem compound slowly went into solution. The mixture was stirred at 55° C. After 1.75 hours, the pH of the mixture was 6.2, and the pH was adjusted upward to 7.3 by addition of dilute sodium hydroxide. After 17.5 hours, the pH of the mixture was 6.1 and was adjusted to 6.95 by addition of dilute sodium hydroxide. The mixture was heated a total of 21 hours. The mixture was cooled in ice, filtered, and the filtrate was adjusted to pH 1.5. A solid precipitated. The solid was filtered, washed with dilute acid (pH 1.5), and air dried to give a light buff colored powder (3.60 g.). The powder was dissolved in 15 ml. of a 2:1 mixture of water and methanol at pH 6.5. The mixture was rotary evaporated to a small volume (about 3 ml.) with isopropyl alcohol being added to avoid frothing toward the end of the rotary evaporation. The residual solution was placed on a Sephadex G-10 (54 g.) column and eluted with water, the first fraction being 25 ml. and all succeeding fractions about 15 ml. Fractions 5–8 were combined, and the pH of the mixture was adjusted to 1.5 by addition of dilute hydrochloric acid. The precipitated product was collected by filtration, washed with dilute acid (pH 1.5), and air dried to give 2.19 g. of 7-α-(t-butoxycarbonylamino)-phenylacetamido-3-(4-methyl-5-oxo-6-hydroxy-4,5-dihydro-1,2,4-triazin-3-ylthio)methyl-3-cephem-4-carboxylic acid as a buff powder.

EXAMPLE 2

The product from Example 1 (404 mg.) was stirred in 4.5 ml. of acetonitrile; however, complete solution was not achieved. p-Toluenesulfonic acid (300 mg.) was added, and within 5 minutes solution was complete, and a solid began to separate. After 1.5 hours, water (0.5 ml.) was added, and the pH of the mixture was adjusted to 5.0 by addition of saturated aqueous ammonium carbonate solution. A major portion of the acetonitrile was removed by rotary evaporation, and isopropyl alcohol was added to the stirred residue until some precipitation became evident. The precipitate was removed by filtration through filter aid. Some tendency to further precipitation was noted upon passage of the solution through the filter aid. The filtrate was stirred and diluted with isopropyl alcohol to give further precipitate which was collected by filtration, washed with a mixture of isopropyl alcohol and water, and air dried to give a buff colored powder (0.18 g.). This powder was mixed with similar material from a larger scale (2.0 g.) reaction, the combined material weighing 1.23 g. This material was stirred in the cold in a mixture of 30 ml. of water and 30 ml. of methanol. The pH of the mixture was slowly adjusted to 7.0 by addition of 1 N aqueous sodium hydroxide. A small amount of insoluble material was removed by filtration. The filtrate was concentrated to about 5 ml. by rotary evaporation, isopropyl alcohol being used in the later stages to prevent frothing. The residual solution was placed on a column of Sephadex G10 (28 g., 1.5 cm.) in water, and 25 ml. fractions were collected, water being used as eluant. Fractions 3–9 were combined. The pH of the combined fractions was adjusted to pH 3.5, and the precipitated product was collected by filtration. The solid was washed with water which had been acidified to pH 3.6 by addition of HCl, and air-dried to give 620 mg. of 7-(α-amino)-phenylacetamido-3-(4-methyl-5-oxo-6-hydroxy-4,5-dihydro-1,2,4-triazin-3-ylthio)methyl-3-cephem-4-carboxylic acid as a light brown powder.

EXAMPLE 3

To 45 ml. of water were added 2.39 g. of 3-mercapto-4-methyl-5-oxo-6-hydroxy-4,5-dihydro-1,2,4-triazine (15 mmole.). The mixture, having a pH of 2.8, was stirred, and the pH was adjusted to 7.25 by addition of 13.4 ml. of 1 N sodium hydroxide. 7-Mandelamido-3-acetoxymethyl-3-cephem-4-carboxylic acid (6.79 g., 15 mmole.) was added, and the pH of the resulting mixture was 3.2. The pH was adjusted to 7.2 by careful addition of 14.8 ml. of 1 N sodium hydroxide. The resulting mixture was heated at 55° C. for 4.25 hours during which the pH of the mixture became 5.85. The pH was increased to 7.17 by addition of 0.7 ml. of 1 N sodium hydroxide. Heating was continued for 14.25 hours during which time the pH of the mixture became 5.99. The mixture was then adjusted to pH 7.09 by addition of 1.45 ml. of 1 N sodium hydroxide. After heating for a total of 20 hours, the mixture was cooled in an ice bath, diluted to about 120 ml. by addition of water, and the pH was adjusted to 1.5 by addition with rapid stirring of 1 N hydrochloric acid. The resulting precipitate was collected by filtration, washed with dilute hydrochloric acid (pH 1.5), and air dried to give an off-white powder (5.28 g.).

This material was stirred in water (40 ml.) during which time the pH of the mixture was adjusted to 6.7 by addition of 1 N sodium hydroxide. The resulting solution was concentrated by addition of isopropyl alcohol and rotary evaporation until the isopropyl alcohol was removed. The final volume of the mixture was about 10 ml. The mixture was placed on a column of Sephadex G-10 (110 g., 2.5 cm., in water). The column was eluted with water, and fractions of 15–16 ml. each were collected. Four fractions or combinations of fractions were prepared, specifically, fractions 5–6, fractions 7–8, fraction 9, and fractions 10–12. Each was stirred in the cold, and the pH of each was adjusted to 1.5 by addition of 1 N hydrochloric acid. A precipitate formed in each and each was collected by filtration, washed with dilute acid (pH 1.5), and air dried to give off-white powders (fractions 5–6—1.26 g.), (fractions 7–8—0.84 g.), (fraction 9—0.31 g.), and fractions 10–12—0.41 g.). Thin-layer chromatography (TLC) showed each product to be identical, and all were combined to give 2.82 g. of an off-white powder.

This material was dissolved in water, and the solution was acidified to pH 1.5. The precipitate was filtered and air dried to give an off-white powder. The powder was dissolved in 25 ml. of tetrahydrofuran, and isopropyl alcohol was added with stirring until a total volume of 200 ml. was obtained. The mixture was filtered. To the filtrate were added 50 ml. of isopropyl alcohol. The mixture was stirred and filtered. The filtrate was evaporated in dryness, and the residue was dissolved in water in pH 7. The solution was acidified to pH 1.5, filtered and air dried to obtain 7-mandelamido-3-(4-methyl-5-oxo-6-hydroxy-4,5-dihydro-1,2,4-triazin-3-ylthio)methyl-3-cephem-4-carboxylic acid as the desired product.

EXAMPLE 4

To 20 ml. of water were added 3.46 g. of 7-formamido-3-acetoxymethyl-3-cephem-4-carboxylic acid (12.0 mmole) and 2.0 g. of 3-mercapto-4-methyl-5-oxo-6-hydroxy-4,5-dihydro-1,2,4-triazine (12.55 mmole). The resulting mixture was stirred, and 1 N sodium hydroxide was added gradually until the pH remained at a constant 7.0. The resulting mixture was then stirred at about 55° C. for 26 hours. The resulting solution was concentrated to 20 ml. and acidified to pH 1.2 by addition with cooling of 3 N hydrochloric acid. The resulting precipitate was filtered and immediately placed into a bell jar to dry under vacuum. The dried material was ground in a mortar and pestle (2.75 g.), and was triturated three times, each with 150 ml. of boiling isopropyl alcohol. The isopropyl alcohol solution was evaporated to dryness and the residue was triturated twice with 30 ml. of ethyl acetate. The insoluble material was filtered, washed with ethyl acetate, and dried to give 1.56 g. of 7-formamido-3-(4-methyl-5-oxo-6-hydroxy-4,5-dihydro-1,2,4-triazin-3-ylthio)methyl-3-cephem-4-carboxylic acid.

EXAMPLE 5

The product from Example 4 (0.74 g.) was stirred in 12 ml. of dry methanol, and 1.5 ml. of concentrated hydrochloric acid were added during which time complete solution occurred. After a short period of time, a white solid began to precipitate. Stirring was continued for 1.7 hours, and the mixture became thick with a white precipitate. The precipitate was filtered and dried. The product (0.346 g.) was shown by TLC to be a highly pure sample of the hydrochloride of 7-amino-3-(4-methyl-5-oxo-6-hydroxy-4,5-dihydro-1,2,4-triazin-3-ylthio)methyl-3-cephem-4-carboxylic acid.

EXAMPLE 6

To 36 ml. of water were added 1.44 g. (9 mmole) of 3-mercapto-4-methyl-5-oxo-6-hydroxy-4,5-dihydro-1,2,4-triazine. The pH of the resulting mixture was 2.9 and was adjusted to 7.20 by addition of 8.7 ml. of 1 N sodium hydroxide. To the mixture were added 3.77 g. (9 mmole) of the sodium salt of 7-(2-thienyl)acetamido-3-acetoxymethyl-3-cephem-4-carboxylic acid. The pH of the resulting mixture was 6.8 and was adjusted to 7.12 by addition of 2 drops of 1 N sodium hydroxide. The mixture was stirred at 55° C. for 4.25 hours during which time the pH changed to 6.03. The pH was raised to 7.10 by addition of 0.3 ml. of 1 N sodium hydroxide. The mixture was heated at 55° C. for an additional 14.25 hours during which time the pH changed to 6.02. The pH then was increased to 7.09 by addition of 0.8 ml. of 1 N sodium hydroxide, and heating was continued for 1.5 hours (total time at 55° C. being 20 hours). The resulting reaction mixture then was stirred in ice water, and the pH was lowered to 1.5 by addition of 1 N hydrochloric acid. A solid formed and was collected by filtration, washed with dilute acid (pH 1.5), and air dried to give a buff colored powder (3.51 g.).

The solid was stirred in 25 ml. of water, and 10 ml. of methanol were slowly added. The pH of the resulting mixture was adjusted to 6.8 by addition portionwise of 1 N sodium hydroxide with intervening sonication of the resulting mixture. The resulting solution was concentrated to about 5 ml. by rotary evaporation, thereby removing the methanol from the mixture, and the concentrate was placed on a column of Sephadex G-10 (70 g., 2 cm. column in water). The column was eluted with water, 10–12 ml. fractions being collected. Fractions 3–5, fractions 6–7, and fractions 8–10 were combined, and the resulting three portions were stirred in the cold, and the pH of each was adjusted to 1.5 by addition of 1 N hydrochloric acid. The resulting three precipitates were collected by filtration, washed with dilute hydrochloric acid (pH 1.5), and air dried to give off-white powders, 2.13 g., 0.69 g., and 0.17 g., respectively. TLC of each of the products indicated that they were virtually identical. The products therefore were combined and dissolved by stirring and boiling in a large volume (about 1200 ml.) of acetone, and the resulting solution was allowed to evaporate to give 1.943 g. of crystalline 7-(2-thienyl)acetamido-3-(4-methyl-5-oxo-6-hydroxy-4,5-dihydro-1,2,4-triazin-3-ylthio)methyl-3-cephem-4-carboxylic acid.

EXAMPLE 7

To 20 ml. of water was added 0.96 g. of 3-mercapto-4-ethyl-5-oxo-6-hydroxy-4,5-dihydro-1,2,4-triazine. The pH of the resulting mixture was 2.3 and was adjusted to 6.5 by addition of 5 ml. of 1 N sodium hydroxide. To the mixture were added 2.09 g. (5 mmole) of the sodium salt of 7-(2-thienyl)acetamido-3-acetoxymethyl-3-cephem-4-carboxylic acid. The pH of the resulting mixture was 5.7 and was adjusted to 7.2 by addition of 1 N sodium hydroxide. The resulting mixture was stirred at 60° C. for a total of 18 hours, the final pH being 5.9. The mixture was cooled in ice and stirred, diluted to about 10 ml., and the pH of the mixture was adjusted to 1.5 by addition of 1 N hydrochloric acid. The resulting solid was collected by filtration, washed with dilute HCl (pH 1.5), and air dried to give an off-white powder (2.01 g.). The material was dissolved at pH 6.8 in 20 ml. of a 1:1 mixture of water and methanol. The solution was evaporated on a rotary evaporation to a small volume (about 3 ml.), and the residual solution was placed on a Sephadex G-10 column (40 g., 1.6 cm. column). The column was eluted with water, the first fraction being about 18 ml. and subsequent fractions about 5 ml. Fractions 4–11 were combined, and the pH was lowered to 1.5 by addition of dilute hydrochloric acid to give 1.171 g. of solid. The solid was dissolved in about 30 ml. of a 3:1 mixture of acetone and methanol. Air was blown over the surface of the solution to evaporate the solution. The resulting crystals of 7-(2-thienyl)acetamido-3-(4-ethyl-5-oxo-6-hydroxy-4,5-dihydro-1,2,4-triazin-3-ylthio)methyl-3-cephem-4-carboxylic acid were filtered and acetone washed.

EXAMPLE 8

To 12 ml. of water were added with stirring 531 mg. (3 mmol.) of 3-mercapto-4-methyl-5-oxo-6-hydroxy-4,5-dihydro-1,2,4-triazine. The pH of the resulting mixture was 2.3 and was adjusted to 6.5 by addition of 2.9 ml. of 1 N sodium hydroxide. 7-(2,5-Dichlorophenylthio)acetamido-3-acetoxymethyl-3-cephem-4-carboxylic acid (1.54 g., 3 mmol.) was added with stirring and resultant formation of a gelatinous mass. The mixture was heated to 60° C. Solution occurred, and, while maintaining the mixture at this temperature, the pH was adjusted to 7.0, and the mixture was maintained thereat for 19 hours. After the first 16 hours, the mixture was thick and gelatinous, so much so that stirring had stopped. The mixture was thoroughly mixed with a spatula, and heating without stirring was continued for the remaining three hours. On completion of heating, the mixture was cooled in an ice bath and acidified to pH 1.5. Fluidity of the mixture was maintained by dilution to about 100 ml. by addition of water. After stirring at pH 1.5 at room temperature for 1.5 hours, the mixture was filtered, washed with dilute HCl (pH 1.5), and air dried to give a cream-colored powder. The powder was dissolved in tetrahydrofuran (THF), filtered, and diluted with ethanol. The resulting solution was placed in an air stream by means of which solid was deposited followed by a yellow gum. The gum was removed with a spatula. The resulting concentrate was filtered, and the product was washed with ethanol and air dried to give an off-white solid (861 mg.). The recrystallization procedure was repeated to give 707 mg. of 7-(2,5-dichlorophenylthio)acetamido-3-(4-methyl-5-oxo-6-hydroxy-4,5-dihydro-1,2,4-triazin-3-ylthio)methyl-3-cephem-4-carboxylic acid as an off-white powder.

EXAMPLE 9

To 12 ml. of water were added with stirring 571 mg. of 3-mercapto-4-ethyl-5-oxo-6-hydroxy-4,5-dihydro-1,2,4-triazine. The pH of the resulting mixture was 2.3 and was adjusted to 6.6 by addition of 2.9 ml. of 1 N sodium hydroxide. 7-(2,5-Dichlorophenylthio)acetamido-3-acetoxymethyl-3-cephem-4-carboxylic acid, sodium salt (1.54 g., 3 mmol.) was added, and the resulting mixture was treated in accordance with the procedure described in Example 8 to obtain 7-(2,5-dichlorophenylthio)acetamido-3-(4-ethyl-5-oxo-6-hydroxy-4,5-dihydro-1,2,4-triazin-3-ylthio)methyl-3-cephem-4-carboxylic acid.

EXAMPLE 10

To 12 ml. of dry THF were added 350 mg. (0.695 mmol.) of 7-(α-amino)phenylacetamido-3-(4-methyl-5-oxo-6-hydroxy-4,5-dihydro-1,2,4-triazin-3-ylthio)methyl-3-cephem-4-carboxylic acid followed by 917 mg. (7 mmol.) of N-trimethylsilylacetamide. Upon completion of the solution, 1 ml. of propylene oxide was added followed by 75 mg. (0.75 mmol.) of N-(p-chlorobenzoyl)-N-(chloroformyl)methylamine dissolved in 2 ml. of dry THF. The addition was made while the mixture was maintained at a temperature of −10° C. The resulting mixture was stirred at −10° C. for 10 minutes and then at room temperature for 15 minutes. Water (1 ml.) was then added followed by 30 ml. of aqueous sodium bicarbonate solution. The mixture then was washed with 50 ml. of a 6:1 mixture of ethyl acetate and THF. The pH of the aqueous layer was lowered to 2.0 by addition of 1 N HCl in the presence of 50 ml. of a 6:1 mixture of fresh ethyl acetate and THF. The organic layer was separated and dried over magnesium sulfate. The mixture then was filtered and evaporated to dryness. The powder residue then was dissolved in warm ethyl acetate, and the ethyl acetate solution was concentrated until it became cloudy. Isopropyl alcohol then was added, complete solution being achieved, and the mixture was again concentrated until the solution became cloudy. The concentrated solution was refrigerated overnight to obtain 234 mg. of 7-α-[3-(4-chlorobenzoyl)-3-methyl-1-ureido]phenylacetamido-3-(4-methyl-5-oxo-6-hydroxy-4,5-dihydro-1,2,4-triazin-3-ylthio)-methyl-3-cephem-4-carboxylic acid.

EXAMPLE 11

To 10 ml. of dry THF were added 379 mg. (0.75 mmol.) of 7-(α-amino)phenylacetamido-3-(4-methyl-5-oxo-6-hydroxy-4,5-dihydro-1,2,4-triazin-3-ylthio)methyl-3-cephem-4-carboxylic acid and 586 mg. (4.5 mmol.) of N-trimethylsilylacetamide. The mixture was stirred at room temperature for 2 hours. Upon completion of solution, 1 ml. of propylene oxide was added, and the solution was cooled to 0° C. N-(o-Chlorobenzoyl)-N-(chloroformyl)methylamine (239 mg., 1.03 mmol.) dissolved in 5 ml. of dry THF was then added dropwise, and the reaction mixture was stirred for 30 minutes at 0° C. and for one hour at room temperature. Five ml. of water were then added, and the THF was removed in vacuo. To the residue then were added 50 ml. of an aqueous sodium bicarbonate solution. The resulting mixture was washed with ethyl acetate, and the pH of the aqueous layer was lowered to 2.0 by addition of 1 N HCl. The acidified aqueous mixture then was extracted with 100 ml. of a 6:1 mixture of ethyl acetate and THF. The organic layer was separated, dried over magnesium sulfate, filtered, and the filtrate was evaporated to dryness. The resulting foam residue was dissolved in ethyl acetate, and ether was added to precipitate 140 mg. of 7-α-[3-(2-chlorobenzoyl)-3-methyl-1-ureido]-phenylacetamido-3-(4-methyl-5-oxo-6-hydroxy-4,5-dihydro-1,2,4-triazin-3-ylthio)methyl-3-cephem-4-carboxylic acid, which was collected by filtration.

EXAMPLE 12

To 20 ml. of dry THF were added 350 mg. (0.695 mmol.) of 7-(α-amino)phenylacetamido-3-(4-methyl-5-oxo-6-hydroxy-4,5-dihydro-1,2,4-triazin-3-ylthio)methyl-3-cephem-4-carboxylic acid followed by 786 mg. (6 mmol.) of N-trimethylsilylacetamide. The resulting mixture was stirred at room temperature for 2 hours during which time solution resulted. Furoyl-2-isocyanate (97.5 mg., 0.71 mmol.) was then added, and the reaction mixture was stirred for 1 hour at room temperature. Water (20 ml.) then was added to the solution. The mixture was reduced in volume until a cloudiness developed at which time 40 ml. of aqueous sodium bicarbonate solution were added. The solution became clear and was washed twice with 50 ml. of ethyl acetate. The aqueous layer was separated, and the pH was lowered to 2.0 by addition of 1 N HCl. The layer was then extracted twice with 50 ml. of ethyl acetate. The ethyl acetate extracts were combined, dried over magnesium sulfate, filtered and evaporated to a foam residue. The residue was dissolved in warm ethanol, and the ethanol solution was concentrated until a cloudiness developed. The thus-concentrated ethanol solution was then refrigerated to obtain, upon filtration, 152 mg. of 7-α-(3-furoyl-1-ureido)phenylacetamido-3-(4-methyl-5-oxo-6-hydroxy-4,5-dihydro-1,2,4-triazin-3-ylthio)methyl-3-cephem-4-carboxylic acid.

EXAMPLE 13

A mixture of 381 mg. (1 mmole) of 7-(1H-tetrazoleacetamido)-3-acetoxymethyl-3-cephem-4-carboxylic acid, 200 mg. (1.2 mmole) of 3-mercapto-4-methyl-5-oxo-6-hydroxy-4,5-dihydro-1,2,4-triazine, and 1.25 mmole of sodium bicarbonate in 30 ml. of pH 7 buffer was prepared. A small amount of solid remained insoluble in the mixture, the pH of the resulting mixture being about 6.6. The mixture was warmed at about 64° C. During the first hour, the pH of the mixture rose to 7.5 and then progressively lowered to about 6.7. Heating was continued for an additional five hours during which time no further pH change occurred. The mixture then was cooled, layered with ethyl acetate, and the pH of the mixture was lowered to 2.7 by addition of 20 percent hydrochloric acid. The organic layer was separated, and the aqueous layer then was washed with additional ethyl acetate. The original ethyl acetate layer as well as the ethyl acetate washes were combined, and the total mixture was dried over magnesium sulfate, filtered, and evaporated to give 100 mg. of 7-(1H-tetrazoleacetamido)-3-(4-methyl-5-oxo-6-hydroxy-4,5-dihydro-1,2,4-triazin-3-ylthio)methyl-3-cephem-4-carboxylic acid, melting point 192°–194° C.

UV $\lambda_{max}$ 273 (Epsilon=14,900).

EXAMPLE 14

To 50 ml. of dry tetrahydrofuran (THF) were added 1.85 g. (5 mmole) of 7-amino-3-(4-methyl-5-oxo-6-hydroxy-4,5-dihydro-1,2,4-triazin-3-ylthio)methyl-3-cephem-4-carboxylic acid and 3.6 ml. (15 mmole) of N,O-bis-trimethylsilylacetamide. The mixture was stirred until solution was complete. The solution then was cooled to −20° C.

Separately, 1.97 g. (5.5 mmole) of the sodium salt of N-(2-methoxycarbonyl-1-methylethenyl)-4-trimethylsilyloxyphenylglycine were added to a solution of 0.085 g. (0.5 mmole) of N-trimethylsilylsuccinimide in 75 ml. of dry tetrahydrofuran. To the resulting mixture were added 6 drops of N,N-dimethylbenzylamine. The resulting suspension then was cooled to −15° C., and 0.52 g. (5.5 mmole) of methyl chloroformate was added with stirring. The mixture was stirred for 15 minutes at −15° C., and the above solution containing the cephalosporin nucleus was added. The resulting reaction mixture was stirred for two hours at −20° C. and then for one hour at room temperature. High pressure liquid chromatography of the reaction mixture indicated the presence of approximately 60 percent of the desired product and 40 percent of the cephalosporin nucleus starting material.

The reaction mixture was worked up by adding 10 ml. of methanol to the mixture. A precipitate formed and was removed by filtration. To the filtrate then were added 10 ml. of water. The mixture was stirred for 15 minutes, and the resulting precipitate was filtered. The filtrate was evaporated in vacuo to about 40 ml., and the concentrated mixture then was cooled overnight in a freezer. A precipitate formed which was collected by filtration.

The resulting collected solid was stirred in 15 ml. of water. The pH of the mixture was adjusted to 1.1 by addition of 3 drops of concentrated hydrochloric acid. The acidic mixture then was stirred for five minutes, and the insolubles were filtered. The pH of the filtrate was raised to 3.0 by addition of sodium hydroxide, and the resulting mixture was stirred for 10 minutes at ice bath temperature. A precipitate formed and was collected by filtration. To the resulting filtrate was added 1 volume of isopropyl alcohol, and the mixture was evaporated in vacuo to about 10 ml. The concentrated solution was stirred in an ice bath for 15 minutes, and the resulting precipitate, 73 mg. of 7-(α-amino-4-hydroxyphenyl)acetamido-3-(4-methyl-5-oxo-6-hydroxy-4,5-dihydro-1,2,4-triazin-3-ylthio)methyl-3-cephem-4-carboxylic acid, was collected by filtration.

EXAMPLE 15

To 25 ml. of dry THF were added 252 mg. (0.5 mmole) of 7-(α-amino)phenylacetamido-3-(4-methyl-5-oxo-6-hydroxy-4,5-dihydro-1,2,4-triazin-3-ylthio)methyl-3-cephem-4-carboxylic acid and 650 mg (5 mmole) of N-trimethylsilylacetamide. The mixture was stirred for about 3 hours after which time solution occurred. The solution then was cooled to 0° C., and 76 mg. (0.5 mmole) of N,N'-dimethyl-N-(chloroformyl)urea were added. The resulting mixture was stirred for one hour at room temperature, and the mixture was evaporated in vacuo to an oil. Water (20 ml.) was added to the oil, and the pH of the resulting mixture was raised to 8.0 by addition of aqueous sodium bicarbonate. The resulting mixture was washed with ethyl acetate, and the pH of the aqueous layer was lowered to 2.0 by addition of 1 N hydrochloric acid. The resulting precipitate was filtered and dried to obtain 118 mg. of 7-α-[3-(N-methylcarbonylamino)-3-methyl-1-ureido]phenylacetamido-3-(4-methyl-5-oxo-6-hydroxy-4,5-dihydro-1,2,4-triazin-3-ylthio)methyl-3-cephem-4-carboxylic acid.

EXAMPLE 16

To 25 ml. of dry THF were added 554 mg. (1.1 mmole) of 7-(α-amino)phenylacetamido-3-(4-methyl-5-oxo-6-hydroxy-4,5-dihydro-1,2,4-triazin-3-ylthio)methyl-3-cephem-4-carboxylic acid and 650 mg. (5 mmole) of N-trimethylsilylacetamide. The mixture was stirred for three hours until solution occurred. The solution then was cooled to 0° C., and 650 mg. (5 mmole) of 1-chloroformylimidazolidine-2-one were added. The resulting mixture was stirred for 30 minutes at 0° C. and then for 1 hour at room temperature. Water (2 ml.) then was added to the mixture. The mixture then was evaporated in vacuo to an oil. Water (25 ml.) was added to the oil, and the pH was raised to 7.5 with sodium bicarbonate. The solution was washed with ethyl acetate, and the aqueous layer then was acidified to pH 1.8 by addition of 1 N hydrochloric acid. The resulting solid was filtered and triturated with methanol, and the methanol insolubles were filtered. The resulting methanol solution was slowly evaporated in vacuo to an oil. Water (25 ml.) was added to the oil, and the pH was raised to 7.5 with sodium bicarbonate. The solution was washed with ethyl acetate, and the aqueous layer then was acidified to pH 1.8 by addition of 1 N hydrochloric acid. The resulting solid was filtered and triturated with methanol, and the methanol insolubles were filtered. The resulting methanol solution was slowly evaporated in vacuo until precipitation resulted. The precipitate was filtered and dried to obtain 92 mg. of 7-α-(imidazolidine-2-one-1-yl-carbonylamino)-phenylacetamido-3-(4-methyl-5-oxo-6-hydroxy-4,5-dihydro-1,2,4-triazin-3-ylthio)methyl-3-cephem-4-carboxylic acid.

EXAMPLE 17

To 20 ml. of dry THF were added 554 mg. (1.1 mmole) of 7-(α-amino)phenylacetamido-3-(4-methyl-5-oxo-6-hydroxy-4,5-dihydro-1,2,4-triazin-3-ylthio)methyl-3-cephem-4-carboxylic acid and 650 mg. (5 mmole) of N-trimethylsilylacetamide. The mixture was stirred for about three hours after which solution was complete. The solution then was cooled to 9° C., and 339 mg. (1.5 mmole) of 1-chloroformyl-3-methanesulfonylimidazolidine-2-one were added. The reaction mixture was stirred for about 30 minutes at 0° C. and then for about 1.5 hours at room temperature. Water (2 ml.) was added to the mixture. The solution then was evaporated in vacuo to an oil. Water (25 ml.) then was added, and the pH of the mixture was raised to 7.5 by addition of sodium bicarbonate. The solution then was washed with ethyl acetate, and the aqueous layer was separated and acidified to pH 1.8 by addition of 1 N hydrochloric acid. The solid which precipitated was filtered and dried to obtain 416 mg. of 7-α-(3-methanesulfonylimidazolidine-2-one-1-ylcarbonylamino)phenylacetamido-3-(4-methyl-5-oxo-6-hydroxy-4,5-dihydro-1,2,4-triazin-3-ylthio)methyl-3-cephem-4-carboxylic acid.

EXAMPLE 18

To 20 ml. of dry tetrahydrofuran (THF) were added 1.53 grams (10 mmole) of hydroxybenzotriazole and 2.57 grams (10 mmole) of α-(t-butoxycarbonylamino)-thien-2-yl-acetic acid. The mixture was cooled to 0° C., and 2.06 grams (10 mmole) of N,N'-dicyclohexylcarbodiimide were added. The mixture was stirred with ice bath cooling for 2.75 hours. The mixture then was filtered rapidly, and the solids were washed with 10 ml. of dry THF. The filtrate which was collected was maintained in an ice bath.

To 60 ml. of dry THF containing 9.8 grams (75 mmole) of N-trimethylsilylacetamide were added 3.73 grams (10 mmole) of 7-amino-3-(4-methyl-5-oxo-6-hydroxy-4,5-dihydro-1,2,4-triazin-3-ylthio)methyl-3-cephem-4-carboxylic acid. The mixture was sonicated for about 1 hour during which time almost complete solution occurred. The resulting solution then was stirred in an ice bath, and, after 15 minutes, was added rapidly to the above-prepared filtrate containing the acylating agent. The resulting mixture was stirred with ice bath cooling for 30 minutes and then at 32° C. for three hours. The resulting brown solution was poured rapidly into stirred ice water. Ether was added, and the pH of the aqueous phase was adjusted to 8.2. The phases were separated, and the water layer was washed with a further volume of ether. The aqueous phase then was subjected to rotary evaporation to remove residual ether. Ice was added to the resulting aqueous solution, and the mixture was stirred rapidly while the pH was adjusted to 1.8 by addition of 1 N hydrochloric acid. The resulting mixture was filtered, and the solid was washed with dilute hydrochloric acid (pH 1.8), air-dried, and dried in vacuo to give 4.16 grams of 7-[α-(t-butoxycarbonylamino)thien-2-ylacetamido]-3-(4-methyl-5-oxo-6-hydroxy-4,5-dihydro-1,2,4-triazin-3-ylthio)-methyl-3-cephem-4-carboxylic acid as a pale, yellow-brown solid.

EXAMPLE 19

The product from Example 18 (1.60 grams) was placed in a flask equipped with a stirrer bar. The flask then was cooled in an ice-acetone bath. To the flask then were added rapidly 60 ml. of trifluoroacetic acid which had first been cooled in an ice-acetone bath. The resulting mixture was stirred for 15 minutes during which time complete solution occurred. Thin-layer chromatography (TLC) of the mixture indicated that the reaction was complete. The reaction mixture then was rotary evaporated to a gum. Ethyl acetate (60 ml.) was added to the gum, and the mixture was sonicated, resulting in a powder which was collected by filtration, washed with ethyl acetate, and air dried to give 1.55 grams of a light brown powder. To the powder was added a mixture of 75 ml. of water and 10 ml. of ethanol. The resulting mixture was sonicated, and the pH was adjusted to 1.4. The mixture was filtered, and the pH of the filtrate was adjusted to 3.7. The resulting mixture was again filtered, and the solid which was collected was washed with dilute acid (pH 3.8) which was added to the filtrate. Isopropyl alcohol then was added to the filtrate and the total was rotary evaporated to a small volume. Additional isopropyl alcohol was added to the residue, and the mixture was filtered. The collected solid was washed with a 1:1 mixture of water and isopropyl alcohol maintained at a pH of 3.8. The resulting solid was dried to obtain 280 mg. of 7-[α-(amino)thien-2-ylacetamido]-3-(4-methyl-5-oxo-6-hydroxy-4,5-dihydro-1,2,4-triazin-3-ylthio)methyl-3-cephem-4-carboxylic acid.

EXAMPLE 20

To 24 ml. of dry tetrahydrofuran were added 408 mg. (0.8 mmole) of the product from Example 19 and 917 mg. (7 mmole) of N-trimethylsilylacetamide. The solution was complete within 10 minutes, and, after 15 minutes, the solution was placed in an ice bath. Propylene oxide (1.6 ml.) and sodium bicarbonate (65 mg.) were added followed by 145 mg. (0.96 mmole; 1.2 mole equivalent) of N-chloroformyl-N,N'-dimethylurea. The resulting mixture was removed from the ice bath and stored at room temperature for 20 minutes. The mixture then was rotary evaporated to a small volume (about 10 ml.), and ice water was added. The resulting suspension then was stirred, and the pH was adjusted to 6.5. The resulting solution was washed with 2 volumes of ether, and the aqueous phase then was rotary evaporated until the ether was removed. The aqueous mixture then was acidified to pH 1.7, and the resulting solid was collected by filtration and partially dried on the filter. The damp product then was dried in vacuo to give 96 mg. of 7-[α-(3-methyl-3-methylaminocarbonyl-1-ureido)thien-2-ylacetamido]-3-(4-methyl-5-oxo-6-hydroxy-4,5-dihydro-1,2,4-triazin-3-ylthio)methyl-3-cephem-4-carboxylic acid as a pale yellow-brown powder.

EXAMPLE 21

Employing the same procedure as described in Example 20, but replacing the N-chloroformyl-N,N'-dimethylurea with 217 mg. (0.96 mmole) of 1-chloroformyl-3-methanesulfonylimidazolidine-2-one gave 242 mg. of 7-[α-(3-methanesulfonylimidazolidine-2-one-1-ylcarbonylamino)thien-2-ylacetamido]-3-(4-methyl-5-oxo-6-hydroxy-4,5-dihydro-1,2,4-triazin-3-ylthio)methyl-3-cephem-4-carboxylic acid.

EXAMPLE 22

To 15 ml. of dry THF were added 317 mg. (0.5 mmole) of the trifluoroacetate salt of 7-(α-amino-4-hydroxyphenylacetamido)-3-(4-methyl-5-oxo-6-hydroxy-4,5-dihydro-1,2,4-triazin-3-ylthio)methyl-3-cephem-4-carboxylic acid. N-Trimethylsilylacetamide (0.59 grams) was added to the resulting suspension. The mixture was stirred for two hours at room temperature after which solution resulted. The mixture then was cooled to 0° C., and 50 mg. of triethylamine and 1 ml. of propylene oxide were added. To the mixture then were added 123 mg. (0.5 mmole) of N-(o-chlorobenzoyl)-N-(chloroformyl)methylamine. The resulting solution then was stirred at room temperature for 1.5 hours after which the reaction mixture was filtered. Water (1 ml.) was added to the filtrate; however, no precipitation occurred. The mixture then was evaporated in vacuo to about 10 ml., and 50 ml. of ethyl acetate were followed by 50 ml. of water. The pH of the mixture was raised to 7.5 by addition of sodium bicarbonate. The ethyl acetate layer then was separated from the aqueous layer. Fresh ethyl acetate (50 ml.) and THF (15 ml.) were added to the aqueous layer, and the pH of the aqueous layer was lowered to 2.5 by addition of 1 N hydrochloric acid. The organic layer was separated from the aqueous, dried over magnesium sulfate, and filtered. The filtrate then was evaporated in vacuo to about 10 ml., and 20 ml. of ether were added. The mixture then was filtered to obtain 150 mg. of 7-[[α-[3-(2-chlorobenzoyl)-3-methyl-1-ureido]-4-hydroxyphenylacetamido]]-3-(4-methyl-5-oxo-6-hydroxy-4,5-dihydro-1,2,4-triazin-3-ylthio)methyl-3-cephem-4-carboxylic acid.

EXAMPLE 23

To 25 ml. of dry THF containing 1.18 grams (9 mmole) of N-trimethylsilylacetamide were added 634 mg. (1.0 mmole) of the trifluoroacetate salt of 7-(α-amino-4-hydroxyphenylacetamido)-3-(4-methyl-5-oxo-6-hydroxy-4,5-dihydro-1,2,4-triazin-3-ylthio)methyl-3-cephem-4-carboxylic acid. Solution occurred within 15 minutes of completion of the addition of the cephalosporin compound. The resulting solution then was cooled to 0° C. in ice-acetone, and 84 mg. (1 mmole) of sodium bicarbonate were added followed by 1 ml. of propylene oxide. To the resulting mixture then were added 226 mg. (1 mmole) of 1-chloroformyl-3-methanesulfonylimidazolidine-2-one. The reaction mixture was warmed to room temperature and stirred at room temperature for 1.5 hours. The reaction mixture then was filtered, and 1 ml. of water was added to the filtrate. No precipitation occurred. The mixture then was evaporated in vacuo to about 10 ml., and 100 ml. of 6:1 mixture of ethyl acetate and THF along with 50 ml. of water were added. The pH of the mixture was raised to 7.0 by addition of sodium bicarbonate. The aqueous layer then was separated from the organic layer, and the pH of the aqueous layer was lowered to 2.0 by addition of 1 N hydrochloric acid. The mixture then was filtered, and the collected solid was washed with isopropyl alcohol and dried to obtain 382 mg. of 7-[α(3-methanesulfonylimidazolidine-2-one-1-ylcarbonylamino)-4-hydroxyphenylacetamido]-3-(4-methyl-5-oxo-6-hydroxy-4,5-dihydro-1,2,4-triazin-3-ylthio)methyl-3-cephem-4-carboxylic acid.

EXAMPLE 24

Using the procedure of Example 22 on a 1 mmole scale, the cephalosporin was reacted with 151 mg. (1 mmole) of N-chloroformyl-N,N'-dimethylurea in the presence of sodium bicarbonate instead of the triethylamine used in Example 22 to obtain 154 mg. of 7-[α-(3-methylaminocarbonyl-3-methyl-1-ureido)-4-hydroxyphenylacetamido]-3-(4-methyl-5-oxo-6-hydroxy-4,5-dihydro-1,2,4-triazin-3-ylthio)methyl-3-cephem-4-carboxylic acid.

EXAMPLE 25

Employing the procedure of Example 24, but employing 1-chloroformylimidazolidine-2-one as acylating agent, there was obtained 120 mg. of 7-[α-(imidazolidine-2-one-1-ylcarbonylamino)-4-hydroxyphenylacetamido]-3-(4-methyl-5-oxo-6-hydroxy-4,5-dihydro-1,2,4-triazin-3-ylthio)methyl-3-cephem-4-carboxylic acid.

EXAMPLE 26

To 100 ml. of dry THF were added 2.54 grams (4 mmoles) of the trifluoroacetate salt of 7-(α-amino-4-hydroxyphenylacetamido)-3-(4-methyl-5-oxo-6-hydroxy-4,5-dihydro-1,2,4-triazin-3-ylthio)methyl-3-cephem-4-carboxylic acid. The resulting suspension was stirred, and 3.66 g. (20 mmoles) of N-trimethylsilylacetamide were added. The mixture was stirred for one hour at room temperature after which solution resulted. The mixture then was cooled in an ice bath, and 548 mg. (4 mmoles) of 2-furoyl isocyanate dissolved in 5 ml. of dry THF were added by syringe. The solution was stirred for one hour at 0° C. and then for one hour at room temperature. Methanol (10 ml.) then was added. Stirring of the mixture for 5 minutes provided no precipitate, and the solution was evaporated to about 30 ml. A mixture of 100 ml. of ethyl acetate and 100 ml. of water was added to the residue, and the pH was raised to 7.5 by addition of sodium bicarbonate. The organic layer was separated from the aqueous layer, and the pH of the aqueous layer was lowered to 2.0 by addition of 1 N hydrochloric acid. The solid which precipitated was filtered, dried, and triturated with ethyl acetate to obtain 660 mg. of 7-[α-(3-furoyl-1-ureido)-4-hydroxyphenylacetamido]-3-(4-methyl-5-oxo-6-hydroxy-4,5-dihydro-1,2,4-triazin-3-ylthio)methyl-3-cephem-4-carboxylic acid, recovered as the ethyl acetate soluble portion.

EXAMPLE 27

To 100 ml. of THF were added 3.29 grams (8.9 mmole) of 7-(α-amino)phenylacetamido-3-(4-methyl-5-oxo-6-hydroxy-4,5-dihydro-1,2,4-triazin-3-ylthio)methyl-3-cephem-4-carboxylic acid and 7.9 grams of N-trimethylsilylacetamide. The resulting mixture was layered with nitrogen and stirred at room temperature for 18 hours during which time solution was achieved.

In a separate vessel, a mixture of 2.36 grams (8.9 mmole) of o-(t-butyloxycarbonylaminomethyl)phenylacetic acid, 1.64 grams (8.9 mmole) of 2,4-dinitrophenol, and 1.84 grams (8.9 mmole) of N,N'-dicyclohexylcarbodiimide in 100 ml. of ethyl acetate was prepared. The resulting mixture was layered with nitrogen and stirred at room temperature for 45 minutes. The resulting precipitate (dicyclohexylurea) was removed by filtration and washed with a small amount of ethyl acetate which was added to the filtrate. The filtrate was evaporated in vacuo to a red-orange gum. The gum was dissolved in 50 ml. of THF, and the solution was added to the previously prepared solution of the cephalosporin trimethylsilyl ester. The resulting mixture was stirred at room temperature for 4 hours after which the solvent was removed in vacuo. The residual gum was dissolved in methanol, and the methanol solution was stirred for 30 minutes, evaporated in vacuo, and the residue was dissolved in 200 ml. of ethyl acetate. The ethyl acetate solution was layered with 200 ml. of water, and the pH was adjusted to 2.5. The organic layer was separated and was washed three times by the above method. The combined aqueous layers then were re-extracted with ethyl acetate; the organic layers were combined, washed two times with saline, dried over magnesium sulfate, filtered, and reduced to a small volume. Upon chilling, the residual volume gave a white precipitate which was removed by filtration and washed with a small portion of cold ethyl acetate. The solid then was dried in vacuo to afford 1.2 grams of 7-(o-t-butyloxycarbonylamino)phenylacetamido-3-(4-methyl-5-oxo-6-hydroxy-4,5-dihydro-1,2,4-triazin-3-ylthio)methyl-3-cephem-4-carboxylic acid.

The above t-butyloxycarbonyl-protected cephalosporin (1.2 grams) was chilled to 0° C. and was dissolved in 50 ml. of cold trifluoroacetic acid. Upon completion of solution, the trifluoroacetic acid was removed in vacuo with the temperature being kept as low as possible (below 0° C.). The resulting gum was dissolved in ethyl acetate, and the ethyl acetate solution was evaporated in vacuo. This was repeated twice to remove excess trifluoroacetic acid. The resulting gum then was dissolved in cold ethyl acetate, and an excess of dry hydrogen chloride (dissolved in ethyl ether) was added. The cold solution was placed under vacuum to remove excess trifluoroacetic acid and hydrogen chloride. The resulting white precipitate was collected by filtration, washed with ethyl acetate, and dried in vacuo to afford 900 mg. of the hydrochloride salt of 7-(o-aminomethyl)-phenylacetamido-3-(4-methyl-5-oxo-6-hydroxy-4,5-dihydro-1,2,4-triazin-3-ylthio)methyl-3-cephem-4-carboxylic acid.

I claim:

1. A compound of the formula

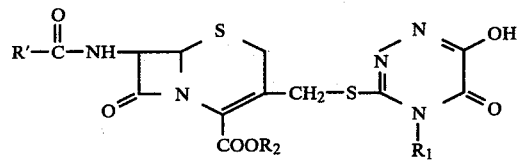

wherein
$R_1$ is hydrogen or lower alkyl;
$R_2$ is hydrogen, an alkali metal cation, or a readily removable ester-forming group;
R' is a group of the formula

wherein P is 2-thienyl, 3-thienyl, 1-tetrazyl, or a phenyl group of the formula

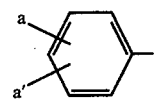

in which a and a' independently are hydrogen, $C_1$–$C_4$ lower alkyl, $C_1$–$C_4$ lower alkoxy, halogen, hydroxy, or aminomethyl; Y is

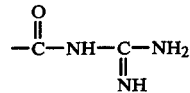

or

wherein R''' is hydrogen or $C_1$–$C_3$ alkyl, and V is phenyl, halophenyl, furyl, mono- or di($C_1$–$C_3$ alkyl)amino, mono- or diphenylamino, or R''' and V taken together form a heterocycle wherein R''' is —(CH$_2$)$_n$— in which n is 2 or 3, and V is —NR'''', in which R'''' is hydrogen, methanesulfonyl, or C$_1$–C$_3$ alkyl.

2. Compound of claim 1, in which R$_2$ is hydrogen or an alkali metal cation.

3. Compound of claim 1, in which R$_1$ is lower alkyl.

4. Compound of claim 3, in which R$_1$ is methyl or ethyl.

5. Compound of claim 3, in which R' is

6. Compound of claim 5, in which P is

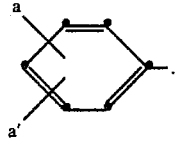

7. Compound of claim 5, in which R' is α-(3-methanesulfonylimidazolidine-2-one-1-ylcarbonylamino)-4-hydroxyphenyl, R$_1$ is methyl, and R$_2$ is hydrogen.

8. Compound of claim 5, in which R' is α-(3-methylaminocarbonyl-3-methyl-1-ureido)-4-hydroxyphenyl, R$_1$ is methyl, and R$_2$ is hydrogen.

9. Compound of claim 5, in which R' is α-(imidazolidine-2-one-1-ylcarbonylamino)-4-hydroxyphenyl, R$_1$ is methyl, and R$_2$ is hydrogen.

10. The compound of claim 5 wherein Y is

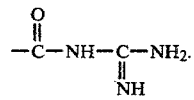

11. The compound of claim 5 wherein Y is

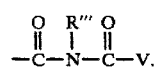

12. The compound of claim 11 wherein V is 4-chlorophenyl, R''' is methyl, and P is phenyl.

13. The compound of claim 11 wherein V is 2-chlorophenyl, R''' is methyl, and P is phenyl or 4-hydroxyphenyl.

14. The compound of claim 11 wherein V is 2-furyl, R''' is hydrogen, and P is phenyl or 4-hydroxyphenyl.

* * * * *